United States Patent [19]

Cliffe

[11] Patent Number: 5,420,278
[45] Date of Patent: May 30, 1995

[54] ω-(4-ARYL OR HETEROARYLPIPERAZINE-1-YL)-2-ARYL OR ARALKYL-PROPANOIC OR BUTANOIC ACIDS

[75] Inventor: Ian A. Cliffe, Slough, England

[73] Assignee: John Wyeth & Brother, Limited, Maidenhead, England

[21] Appl. No.: 248,124

[22] Filed: May 24, 1994

Related U.S. Application Data

[60] Division of Ser. No. 911,996, Jul. 10, 1992, Pat. No. 5,364,849, which is a continuation of Ser. No. 756,932, Sep. 9, 1991, abandoned, which is a continuation-in-part of Ser. No. 511,150, Apr. 19, 1990, abandoned.

[30] Foreign Application Priority Data

Apr. 22, 1989 [GB] United Kingdom ............... 8909209
Oct. 28, 1989 [GB] United Kingdom ............... 8924323

[51] Int. Cl.$^6$ ............... C07D 403/03; C07D 401/04; C07D 295/00; C07D 241/04
[52] U.S. Cl. ............... 544/392; 544/295; 544/357; 544/360; 544/393; 544/394
[58] Field of Search ............... 544/392, 295, 357, 360, 544/393, 394

[56] References Cited

U.S. PATENT DOCUMENTS 4,988,814 1/1991 Abou-Gharbia et al. ........... 544/392
5,246,935 9/1993 Jeppesen et al. ................... 544/392

Primary Examiner—Cecilia Tsang
Attorney, Agent, or Firm—Arthur G. Seifert

[57] ABSTRACT

Piperazine derivatives of formula

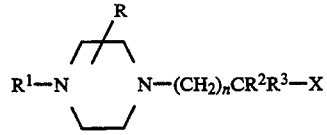

and their pharmaceutically acceptable acid addition salts are disclosed. In the formula n is 1 or 2, R is hydrogen or lower alkyl, $R^1$ is an aryl or nitrogen containing heteroaryl radical, $R^2$ is hydrogen or lower alkyl, $R^3$ is aryl, $C_{4-8}$ alkyl or aryl(lower)alkyl and X is a functionalized group of specified meaning. The compounds exhibit activity as 5-$HT_{1A}$ antagonists and can be used, into alia, for the treatment of CNS disorders, such as anxiety.

5 Claims, No Drawings

ω-(4-ARYL OR HETEROARYLPIPERAZINE-1-YL)-2-ARYL OR ARALKYL-PROPANOIC OR BUTANOIC ACIDS

This application is a division of U.S. patent application Ser. No. 07/911,996, filed on Jul. 10, 1992, now U.S. Pat. No. 5,364,849, which in turn is a continuation of U.S. patent application Ser. No. 07/756,932, filed on Sep. 9, 1991, (abandoned), which in turn is a continuation-in-part of U.S. patent application Ser. No. 511,150, filed on Apr. 19, 1990, (abandoned).

This invention relates to piperazine derivatives, to processes for their preparation, to their use and to pharmaceutical compositions containing them. The novel compounds act on the central nervous system by binding to 5-HT receptors (as more fully explained below) and hence can be used as medicaments for treating humans and other mammals.

The novel compounds of the invention are those of the general formula

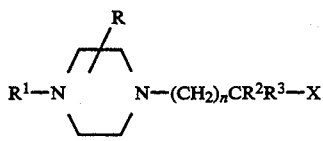

(I)

and the pharmaceutically acceptable acid addition salts thereof.

In formula (I)

n is one of the integers 1 or 2.

R is hydrogen or lower alkyl, $R^1$ is an aryl or monocyclic nitrogen containing heteroaryl radical, $R^2$ is hydrogen or lower alkyl, $R^3$ is an aryl radical, an alkyl radical containing 4 to 8 carbon atoms or an aryl(lower)alkyl radical, X is —$OCOR^{10}$, —$CO_2R^6$, —$CONR^5R^9$, —O-$CO_2R^6$, —$NR^4COR^6$, $OCONHR^{11}$, —$NHCO_2R^6$, —$NR^4CONHR^6$, —$CONHNHR^6$, —$CONHOR^6$,

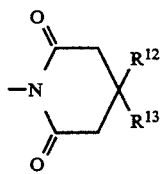

or

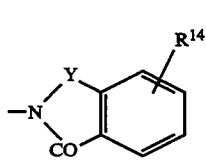

$R^4$ and $R^5$ are each hydrogen or lower alkyl $R^6$ is —$CHR^7R^8$, cycloalkyl of 3 to 12 carbon atoms or aryl(lower)alkyl (where $R^7$ and $R^8$ are each hydrogen or lower alkyl), $R^9$ is hydrogen, an alkyl group of 1 to 8 carbon atoms other than a tertiary alkyl group, cycloalkyl of 3 to 12 carbon atoms, cycloalkyl(lower)alkyl, aryl, aryl(lower)alkyl or 8-azaspiro[4.5]deca-7,9-dione-8-yl-(lower)alkyl [with the proviso that when $R^3$ is aryl or aralkyl, $R^9$ is not a phenyl group substituted in the ortho position by halogen, nitro, trifluoroalkyl, cyano, sulphonic acid, sulphonamido, carboxy, carbalkoxy, carboxylanilino or a 4-carboxyamino-benzosulphonamido group and that when $R^9$ is hydrogen, alkyl, aryl or aryl(lower)alkyl $R^5$ is hydrogen or —$CHR^7R^8$], or $R^5$ and $R^9$ together with the nitrogen atom to which they are attached represent an azetidino, pyrrolidino, piperidino, hexahydroazepino, morpholino or piperazino ring which may be optionally substituted by lower alkyl, aryl or aryl(lower)alkyl $R^{10}$ is cycloalkyl of 3 to 12 carbon atoms, or 2,3-dihydro[1,4]benzodioxinyl optionally substituted by lower alkyl, lower alkoxy or halogen or, when R3 is an alkyl radical containing 4 to 8 carbon atoms, $R^{10}$ can also be aryl;

$R^{11}$ is cycloalkyl of 3 to 12 carbon atoms, aryl or aryl(lower)alkyl, $R^{12}$ and $R^{13}$ are each lower alkyl or together with the carbon atom to which they are both attached represent $C_{4-6}$ cycloalkyl, $R^{14}$ represents hydrogen, halogen, lower alkyl or lower alkoxy and Y is CO or $SO_2$.

The term "lower" as used herein means that the radical referred to contains 1 to 6 carbon atoms. Preferably such radicals contain 1 to 4 carbon atoms. Examples of "lower alkyl" are methyl, ethyl, propyl, isopropyl, butyl, isobutyl, tert.-butyl, pentyl and isopentyl. When $R^3$ is an alkyl group of 4 to 8 carbon atoms it may be a straight or branched chain group; a preferred example is tert.-butyl. Preferably $R^3$ is an aryl radical.

When used herein "aryl" means an aromatic radical having 6 to 12 carbon atoms (eg phenyl, naphthyl) which optionally may be substituted by one or more substituents commonly used in medicinal chemistry, eg substituents such as lower alkoxy, halogen, trifluoromethyl, nitro, carbalkoxy, carboxamido, cyano, amino, (lower)alkylamino and di(lower)alkylamino.

Examples of aryl(lower)alkyl and aryl(lower)alkoxy include, for example, benzyl and benzyloxy in which the phenyl group may be substituted as defined above.

When used herein "nitrogen containing heteroaryl radical" means an aromatic ring containing one or more nitrogen atoms as heteroatoms (eg pyridinyl, pyrimidinyl or pyrazinyl) which may optionally be substituted by one or more lower alkyl, lower alkoxy, halogen, trifluoromethyl, amino, (lower)alkylamino or di(lower)alkylamino substituents. Preferably the heteroaryl radical is monocyclic.

Preferred compounds are:

those in which n is 1;

those in which $R^1$ is aryl particularly an optionally substituted phenyl such as o-methoxyphenyl;

those in which R is hydrogen;

those in which $R^2$ is hydrogen;

those in which $R^3$ is aryl particularly optionally substituted phenyl;

those in which X is an ester grouping of formula —$CO_2R^6$ or an amide grouping of formula —$CONR^5R^9$ particularly where —$NR^5R^9$ represents a cyclic grouping eg piperidino or hexahydroazepino.

The compounds of the invention may be prepared by a number of methods known in the art from known starting materials or starting materials that may be prepared by conventional methods. In one method for preparing an amide of formula (I), where X represents —CONR$^5$R$^9$ an amine of formula

NHR$^5$R$^9$         (II)

where R$^5$ and R$^9$ are as defined above is acylated with an acid of formula

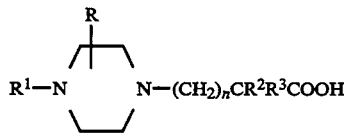    (III)

(where R, R$^1$, R$^2$ and R$^3$ are as defined above) or with an acylating derivative thereof. Examples of acylating derivatives include the acid halides (eg acid chlorides), azides, anhydrides, imidazolides (eg obtained from carbonyldiimidazole), activated esters or O-acyl ureas obtained from a carbodiimide such as a dialkylcarbodiimide particularly dicyclohexylcarbodiimide. Preferably the amine is acylated with the acid in presence of a coupling agent such as 1,1'-carbonyldiimidazole, isobutylchloroformate or diphenylphosphinyl chloride.

The acids of formula III are novel compounds and are also provided by this invention.

The reverse amides, ie the compounds of the invention in which X is —NR$^4$COR$^6$ may be prepared in an analogous manner to the amides mentioned above by acylating the piperazine alkylamine

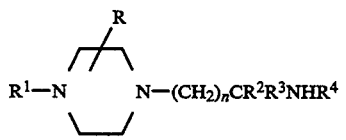

with an acid of formula

R$^6$COOH or with an acylating derivative thereof.

Similarly, the compounds of the invention in which X is

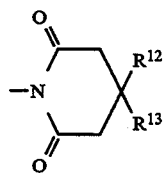

or

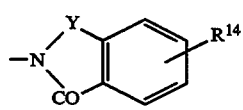

may be prepared by reacting an amine of formula

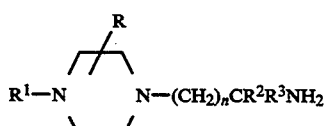

with an anhydride of formula

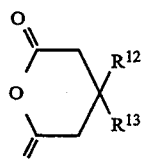

or

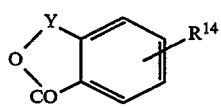

or with an acid of formula

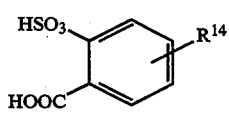

An ester of the invention in which —X is —CO$_2$R$^6$ may be prepared by esterification of the acid of formula (III) above with an alcohol of formula R$^6$OH.

The reverse esters, ie the compounds in which X is —OCOR$^{10}$, may be prepared by esterifying a piperazine alcohol of formula

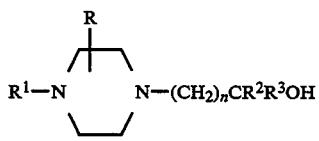

with an acid of formula R$^{10}$COOH.

Both types of esterification may be carried out by methods known in the art. For example an acid halide may be reacted with the appropriate alcohol.

The ureas, ie compounds in which X is —NR$^4$CONHR$^6$ and the carbamates, ie compounds in which X is —O.CO.NHR$^{11}$ may be prepared by reacting the piperazinyl-alkanol or -alkylamine of formula

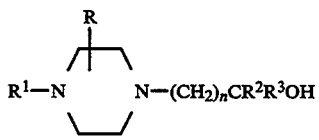

or

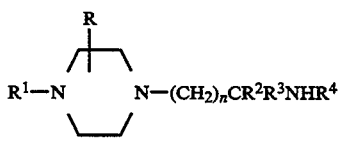

with the appropriate isocyanate. The reverse carbamates, ie the compounds in which X is —NHCO$_2$R$^6$ may be prepared in a similar manner from the piperazine isocyanate derivative

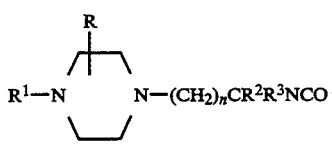

and the alcohol R⁶OH, or by reacting an amine of formula

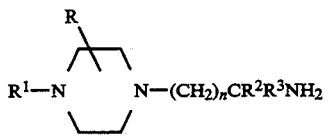

with a compound of formula R⁶OCOHal (where Hal is halogen, eg chlorine).

The hydroxylamine compounds of the invention, ie compounds in which X is CONHOR⁶ may be prepared by reacting the acid of formula (III) above with a hydroxylamine of formula NH₂OR⁶.

The hydrazide compounds of the invention, ie compounds in which X is —CONHNHR⁶ may be prepared by reacting the acid of formula (III) with a hydrazide of formula NH₂NHR⁶.

An alternative method of preparing the compounds of the invention comprises alkylation of a piperazine of formula

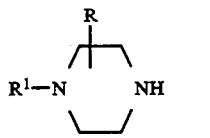 (IV)

(where R and R¹ are as defined above) with an alkylating agent providing the group

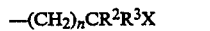 (V)

(where n, R², R³ and X are as defined above).

The alkylating agent may be, for example, a compound of formula

Z—CH₂CR²R³X (VI)

where R², R³ and X are as defined above and Z is a leaving group such as halogen or an alkyl- or aryl-sulphonyloxy group. Alternatively the alkylating agent may be an unsaturated compound of formula

CH₂=CR³X (VII)

(where R³ and X are as defined above) and the compound of formula (VII) is reacted with the piperazine of formula (IV) by means of a Michael reaction. The reaction may be carried out at elevated temperature in the presence of an alcohol. A small quantity of an acid catalyst may be employed in the reaction when X represents —CONR⁵R⁹.

The starting materials for the processes described above may be prepared by methods known in the art. For example certain acids of formula (III) may be prepared by Michael reaction of an acid of formula

CH₂=CR³COOH (VIII)

and a piperazine of formula

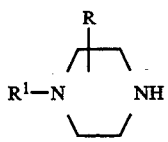 (IV)

in a method similar to the Michael reaction described above. The unsaturated compound of formula (VII) may be prepared from the acid of formula (VIII) by the known methods of obtaining amides and esters from acids. In a preferred method the acid is reacted with an amine in the presence of a condensing agent such as isobutylchloroformate or the acid is esterified, eg by reaction with an alcohol in presence of 2-chloro-1-methylpyridinium iodide. The acids of formula (VIII) are known or may be prepared by methods known in the art.

The amides of formula (I) in which X is —CONR⁵R⁹ where R⁵ is hydrogen and R⁹ is a secondary (lower)alkyl group may be prepared by an alternative method comprising reacting a nitrile of formula

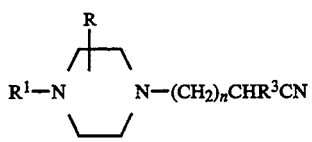 (IX)

with a secondary alcohol under acidic conditions as in the Ritter reaction. The nitrile (IX) may also be subjected to acid hydrolysis to give an amide of formula (I) in which X is CONH₂. Furthermore the nitrile may be hydrolysed to the acid (III) which may then be converted to compounds of formula (I) by the methods given above. The nitrile of formula (IX) may be prepared by known methods such as reacting an unsaturated nitrile of formula CH₂=CR³CN with a piperazine of formula (IV) Under Michael conditions or reacting a ketone of formula

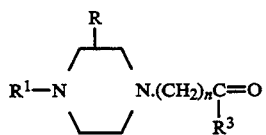 (X)

with p-toluenesulphonylisocyanide.

A further method of preparing the amides of formula (I) in which X is —CONHR⁹ comprises the desulphurisation of a sulphur containing compound of formula

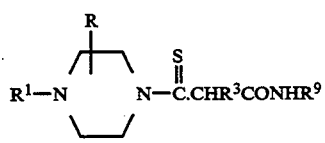 (XI)

where R, R¹ and R⁹ are as defined above and R³ is aryl. The desulphurisation may be carried out in presence of a-nickel catalyst. The compound of formula (XI) may be prepared by a Willgerodt reaction, eg an aryl alkyl ketone of formula CH₃CO.R³ is reacted with sulphur and a piperazine of formula (IV) and the resulting thioamide is treated with a base and with a isocyanate of formula R⁹NCO.

The processes described above may be carried out to give a compound of the invention in the form of a free base or as an acid addition salt. If the compound of the invention is obtained as an acid addition salt, the free base can be obtained by basifying a solution of the acid addition salt. Conversely, if the product of the process is a free base an acid addition salt, particularly a pharmaceutically acceptable acid addition salt, may be obtained by dissolving the free base in a suitable organic solvent and treating the solution with an acid, in accordance with conventional procedures for preparing acid addition salts from base compounds.

Examples of acid addition salts are those formed from inorganic and organic acids, such as sulphuric, hydrochloric, hydrobromic, phosphoric, tartaric, fumaric, maleic, citric, acetic, formic, methanesulphonic, p-toluenesulphonic, oxalic and succinic acids.

The compounds of the invention may contain one or more asymmetric carbon atoms, so that the compounds can exist in different steroisomeric forms. The compounds can be for example, racemates or-optically active forms. The optically active forms can be obtained by resolution of the racemates or by asymmetric synthesis.

The compounds of the present invention possess pharmacological activity. In particular, they act on the central nervous system by binding to 5-HT receptors. In pharmacological testing it has been shown that the compounds particularly bind to receptors of the 5-$HT_{1A}$ type. In general, the compounds selectively bind to receptors of the 5-$HT_{1A}$ type to a much greater extent than they bind to other receptors such as $\alpha_1$ and $D_2$ receptors. Many exhibit activity as 5-$HT_{1A}$ antagonists in pharmacological testing. The pharmacological testing of the compounds indicates that they can be used for the treatment of CNS disorders, such as anxiety in mammals, particularly humans. They may also be useful as antidepressants, hypotensives and as agents for regulating the sleep/wake cycle, feeding behaviour and/or sexual function.

The compounds of the invention were tested for 5-$HT_{1A}$ receptor binding activity in rat hippocampal membrane homogenate by the method of B. S. Alexander and M. D. Wood, J Pharm Pharmarol, 1988, 40, 888–891. The results for representative compounds of the invention are given below.

| Compounds of Example | IC$_{50}$ (nM) |
|---|---|
| 6 | 127 |
| 8 | 45 |
| 19 | 24 |
| 21 | 49 |
| 22 | 45 |
| 23 | 59 |
| 24 | 75 |
| 26 | 46 |
| 29 | 25 |
| 31 | 28 |
| 32 | 21 |
| 33 | 8 |
| 34 | 9 |
| 35 | 16.5 |
| 37 | 45 |
| 39 | 22 |
| 40 | 78 |
| 42 | 88 |
| 43 | 37 |

-continued

| Compounds of Example | IC$_{50}$ (nM) |
|---|---|
| 59 | 3 |

The affinity for $D_2$ receptor sites (as measured by the procedure of A. A. Hancock et al, Mol Pharmacol, 1984, 26, 439) and for $\alpha_1$ sites (as measured by the procedure of A. L. Morrow et al, Mol Pharmacol, 1986, 29, 321) for various compounds is given below:

| Compound of Example | Affinity for $D_2$ site IC$_{50}$ (nM) | Affinity for $\alpha_1$ site IC$_{50}$ (nM) |
|---|---|---|
| 19 | 6290 | 976 |
| 21 |  | 1200 |
| 22 |  | 1230 |
| 24 |  | >104 |
| 26 |  | 1090 |
| 29 |  | 1140 |
| 32 | >10000 | 851 |
| 37 |  | 7310 |
| 42 |  | 2850 |
| 43 |  | 988 |

The compounds are tested for 5-$HT_{1A}$ receptor antagonism activity in a test involving the antagonism of 5-carboxamidotryptamine in the guine-pig ileum in in vitro (based upon the procedure of Fozard et al, Br J Pharmac, 1985, 86, 601P). The results for compounds of the invention are given below.

| Compound of Example | pA$_2$ |
|---|---|
| 19 | 6.9 |
| 21 | 6.9 |
| 23 | 7.0 |
| 26 | 6.8 |
| 31 | 7.4 |
| 32 | 6.8 |
| 37 | 7.6 |
| 43 | 6.9 |

The invention also provides a pharmaceutical composition comprising a compound or a pharmaceutically acceptable acid addition salt thereof in association with a pharmaceutically acceptable carrier. Any suitable carrier known in the art can be used to prepare the pharmaceutical composition. In such a composition, the carrier is generally a solid or liquid or a mixture of a solid or liquid.

Solid form compositions include powders, granules, tablets, capsules (eg hard and soft gelatine capsules), suppositories and pessaries. A solid carrier can be, for example, one or more substances which may also act as flavouring agents, lubricants, solubilisers, suspending agents, fillers, glidants, compression aides, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, eg from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilisers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above, eg cellulose derivatives, preferably sodium carboxymethyl cellulose solution), alcohols, eg glycerol and glycols) and their derivatives, and oils (eg fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, eg as tablets or capsules. In such form, the composition is sub-divided in unit dose containing appropriate quantities of the active ingredient; the unit dosage forms can be packaged composition, for example packeted powders, vials, ampoules, prefilled syringes or sachets containing liquid. The unit dosage form can be, for example, a capsule or tablet itself, or it can be the appropriate number of any such compositions in package form. The quantity of the active ingredient in unit dose of composition may be varied or adjusted from 0.5 mg or less to 750 mg or more, according to the particular need and the activity of the active ingredient.

The following Examples illustrate the invention:

EXAMPLE 1

α-{1-[4-(2-Methoxyphenyl)piperazinyl]methyl}-benzeneacetic acid 1-(2-Methoxyphenyl)piperazine (22.6 g; 0.118 mol) and atropic acid (174 g, 0.118 moll in ethanol (300 ml) were heated under reflux for 18 hours, cooled to room temperature, and evaporated in vacuo. The solid was triturated with acetone (3×100 ml) to give a first crop of product (13.8 g) as white crystals. The filtrate was evaporated in vacuo to give an oil which slowly crystallised over 1 month. The solid was triturated with acetone (200 ml) to give a second crop of the hemihydrate of the product (9.01 g) as white crystals, m.p. 160°–163°. (Found: C, 68.4; H, 7.2; N, 7.9. $C_{20}H_{24}N_2O_3 \cdot 0.5H_2O$ requires C, 68.8; H, 7.2; N, 8.0%.)

EXAMPLE 2

2-{1-[4-(2-Methoxyphenyl)piperazinyl]methyl}-3-benzenepropanoic acid 2-(Phenylmethyl)propenoic acid (Mannich and Ganz, Chem. Ber., 1922, 55, 34867) (2.00 g, 12.35 mmol) and 1-(2-methoxyphenyl)piperazine (2.37 g, 12.35 mmol) in propanol (25 ml) were heated under reflux for 18 hours, cooled to room temperature, and evaporated in vacuo. The residue was triturated with acetone and ether to give the product (0.80 g) as a colourless powder, m.p. 155°–158°. (Found: C, 71.6; H, 7.4; N, 7.6. $C_{21}H_{26}N_2O_3$ requires C, 71.2; H, 7.3; N, 7.9%.)

EXAMPLE 3

2-Phenyl-N-(phenylmethyl)propenamide

A stirred solution of atropic acid (10.3 g, 69.5 mmol) in dry tetrahydrofuran (100 ml) was treated under nitrogen with N-methylmorpholine (7.7 ml, 70.0 mmol), cooled to −10°, treated dropwise with iso-butylchloroformate (9 ml, 69.4 mmol), treated dropwise with benzylamine (7.6 ml, 69.6 mmol), warmed to room temperature over 1 hour, filtered and evaporated in vacuo to give a yellow oil which was dissolved in ether (100 ml). The solution was washed with 0.1N-HCl (200 ml), brine (100 ml), 0.1N-NaOH (100 ml) and brine (100 ml), dried ($MgSO_4$), and evaporated in vacuo to give a yellow liquid. Purification by chromatography (silica; di-iso-propyl ether) gave the product as white crystals (7.3 g), m.p. 84°–86° (from di-iso-propyl ether). (Found: C, 80.8; H, 6.3; N, 5.7. $C_{16}H_{15}NO$ requires C, 81.0; H, 6.4; N, 5.9%.)

EXAMPLE 4

N-Cyclohexyl-2-phenylpropenamide

This compound was made from atropic acid (10.48 g, 70.8 mmol), N-methylmorpholine (7.8 ml, 70.9 mmol), iso-butyl chloroformate (9.2 ml, 70.9 mmol), and cyclohexylamine (8.1 ml, 70.7 mmol) using the procedure described in Example 3. The crude product was purified by recrystallisation from cyclohexane to give the product (4.69 g), as white crystals, m.p. 131°–133°. (Found: C, 78.7; H, 8.8; N, 5.95. $C_{15}H_{19}NO$ requires C, 78.6; H, 8.35; N, 6.1%.)

EXAMPLE 5

Propyl 3-{1-[4-(2-methoxyphenyl)piperazinyl]}-2-phenylpropanoate

A stirred solution of atropic acid (2.11 g, 14.3 mmol) and cyclohexanol (1.51 ml, 14.2 mmol) in ethyl acetate (40 ml) at 2°–5° was treated dropwise with N,N′-dicyclohexylcarbodiimide (3.27 g, 15.8 mmol), warmed to room temperature, filtered and evaporated in vacuo to give a yellow oil.

A solution of the oil in propanol (20 ml) was heated under reflux for 1 day, cooled to room temperature, evaporated in vacuo, and the residue purified by chromatography [silica; ether-hexane (1:3) and silica; di-iso-propyl ether] to give the free base as an oil (1.1 g).

Formation of the salt in the usual manner gave the hydrochloride (0.95 g), m.p. 200°–204°. (Found: C, 60.9; H, 7.25; N, 6.3. $C_{23}H_{30}N_2O_3 \cdot 2HCl$ requires C, 60.7; H, 7.1; N, 6.15%.)

EXAMPLE 6

3-{1-[4-(2-Methoxyphenyl)piperazinyl]}-2-phenyl-N-phenylpropanamide

A solution of the product of Example 1 (1.102 g, 3.2 mmol) in dichloromethane (50 ml) was treated with 1,1'-carbonyldiimidazole (0.58 g, 3.6 mmol), stirred for 1 hour, treated with aniline (0.4 ml, 4.4 mmol), stirred for 18 h, evaporated in vacuo, and the residue purified by chromatography (silica; di-iso-propyl ether→ether). The foam was dissolved in hot propan-2-ol (10 ml) and the solution acidified with ethereal hydrogen chloride. Evaporation in vacuo gave a glass which crystallised upon trituration with ether as the dihydrochloride quarter hydrate salt of the product (0.897 g), m.p. 250°–255° (dec.). (Found: C, 63.4; H, 6.8; N, 8.5. $C_{26}H_{29}N_3O_2.2HCl.\frac{1}{4}H_2O$ requires C, 63.35; 6.4; N, 8.5%.)

EXAMPLES 7–21

The following 3-{1-[4-(2-methoxyphenyl)piperazinyl]}-2-phenylpropanamides were prepared following the procedure of Example 6 but using the indicated amine reactant instead of aniline.

over 3 hours. Evaporation in vacuo and chromatography (silica, ethyl acetate) gave the free base (0.532 g.)

The solid was dissolved in hot methanol (5 ml) and the solution acidified with ethereal hydrogen chloride and evaporated in vacuo to give the dihydrochloride three-quarter hydrate salt of the product (0.581 g) as colourless crystals, mp. 236°–238° (dec.). (Found: C, 58.1; H, 7.4; N, 9.1. $C_{22}H_{29}N_3O_2.2HCl.\frac{3}{4}H_2O$ requires C, 58.2; H, 7.2; N, 9.3%.)

EXAMPLE 23

3-{1-[4-(2-Methoxyphenyl)piperazinyl]}-2-phenyl-N-(phenylmethyl)propanamide

A solution of the product of Example 3 (1.25 g, 5.3 mmol), 1-(2-methoxyphenyl)piperazine (1.00 g, 5.2 mmol), and acetic acid (3 drops) was heated under reflux under an atmosphere of nitrogen for 40 hours, cooled to room temperature, and evaporated in vacuo to give an oil which crystallised from ethyl acetate. A suspension of the crystals in hot propan-2-ol was acidified with ethereal hydrogen chloride. The hot solution was cooled to room temperature and the precipitate filtered and washed with propan-2-ol and ether to give the product (1.94 g), m.p. 211°–214°. (Found: C, 64.5; H, 3-{1-4-(2-Methoxyphenyl)piperazinyl]}-2-phenylpropanamides

| Example | Amine Reactant | Amide Product | Formula | Found % (Required) C | H | N | m.p. (°C.) |
|---|---|---|---|---|---|---|---|
| 7 | $NH_3$—THF | amide | $C_{20}H_{25}N_3O_2 2HCl$ | 58.05 (58.25) | 6.7 (6.6) | 10.2 (10.2) | 194–195 |
| 8 | $MeNH_2$—EtOH (33% W/W) | methylamide | $C_{21}H_{27}N_3O_2 2HCl\frac{3}{4}H_2O$ | 57.6 (57.3) | 7.15 (7.0) | 9.2 (9.55) | 203–205 |
| 9 | $EtNH_2$—EtOH (33% W/W) | ethylamide | $C_{22}H_{29}N_3O_2 2HCl\frac{1}{4}H_2O$ | 59.4 (59.4) | 7.2 (7.1) | 9.5 (9.4) | 204–206 |
| 10 | $PrNH_2$ | propylamide | $C_{23}H_{31}N_3O_2 2HCl$ | 60.6 (60.8) | 7.6 (7.3) | 9.7 (9.25) | 213–215 |
| 11 | $BuNH_2$ | butylamide | $C_{24}H_{33}N_3O_2 2HCl$ | 61.6 (61.5) | 7.8 (7.5) | 9.2 (9.0) | 199–200 |
| 12 | iso-$PrNH_2$ | iso-propylamide | $C_{23}H_{31}N_3O_2 2HCl$ | 60.55 (60.8) | 7.6 (7.3) | 9.6 (9.25) | 221–224 |
| 13 | iso-$BuNH_2$ | iso-butylamide | $C_{24}H_{33}N_3O_2 2HCl$ | 61.4 (61.5) | 7.7 (7.5) | 9.0 (9.0) | 202–203 |
| 14 | $C_3H_5CH_2NH_2$ | cyclopropyl-methylamide | $C_{24}H_{31}N_3O_2 2HCl$ | 61.9 (61.8) | 7.0 (7.1) | 8.7 (9.0) | 200–202 |
| 15 | t-$BuCH_2NH_2$ | neopentylamide | $C_{25}H_{35}N_3O_2 HCl$ | 61.9 (62.2) | 7.6 (7.7) | 8.7 (8.7) | 200–203 |
| 16 | $C_6H_{13}NH_2$ | hexylamide | $C_{26}H_{37}N_3O_2 2HCl$ | 62.5 (62.9) | 7.9 (7.5) | 8.4 (8.5) | 189–190 |
| 17 | $C_6H_{11}CH_2NH_2$ | cyclohexyl-methylamide | $C_{27}H_{37}N_3O_2 2HCl$ | 63.5 (63.8) | 8.0 (7.7) | 8.4 (8.3) | 205–207 |
| 18 | $C_5H_9NH_2$ | cyclopentylamide | $C_{25}H_{33}N_3O_2 2HCl\frac{1}{4}H_2O$ | 62.0 (62.0) | 7.3 (7.4) | 8.9 (8.7) | 213–214 |
| 19 | $C_6H_{11}NH_2$ | cyclohexylamide | $C_{26}H_{35}N_3O_2 2HCl$ | 63.0 (63.15) | 7.8 (7.5) | 8.1 (8.5) | 216–219 |
| 20 | $C_7H_{13}NH_2$ | cycloheptylamide | $C_{27}H_{37}N_3O_2 2HCl$ | 63.6 (63.8) | 7.9 (7.7) | 8.0 (8.3) | 206–208 |
| 21 | $C_{11}H_{18}N_2O_2$[a] | [b] | $C_{31}H_{40}N_4O_4 2HCl$ | 61.4 (61.5) | 7.3 (7.0) | 9.2 (9.25) | 148–152 |

[a] 8-(Aminoethyl)-8-azaspiro[4.5]deca-7,9-dione
[b] The product was 8-{α-{1-[4-(2-methoxyphenyl)piperazinyl]methyl}phenylactamidoethyl}-8-azaspiro[4.5]deca-7,9-dione

EXAMPLE 22

N,N-Dimethyl-3-{1-[4-(2-methoxyphenyl)-piperazinyl]}-2-phenylpropanamide

A stirred solution of the product of Example 1 (1.786 g, 5.2 mmol) and N-methylmorpholine (0.65 ml, 5.9 mmol) in dichloromethane (20 ml) at −30° was treated with diphenylphosphinyl chloride (1.1 ml, 5.8 mmol) under an atmosphere of nitrogen. After 1 hour, 25–30% w/v dimethylamine in water (1.2 ml, ca. 7.5 mmol) was added and the solution warmed to room temperature 7.1; N, 7.9. $C_{27}H_{31}N_3O_2.2HCl$ requires C, 64.5; H, 6.6; N, 8.4%.)

EXAMPLE 24

N-Cyclohexyl-2-phenyl-3-{1-[4-(2-pyrimidinyl)-piperazinyl]}propanamide

A solution of the product of Example 4 (0.90 g, 3.9 mmol) and N-(2-pyrimidyl)piperazine dihydrochloride (0.95 g, 4.0 mmol) in 1 N-NaOH (8.0 ml), propanol (10 ml), and acetic acid (8 drops) was heated under reflux for 48 hours, cooled to room temperature, and concentrated in vacuo. The aqueous residue was diluted with water (50 ml) and extracted with dichloromethane (50 ml). The extracts were washed with water (50 ml), dried (MgSO$_4$), and evaporated in vacuo to give an oil. Purification by column chromatography (alumina; ether) gave the product free base (0.63 g) as colourless crystals.

The crystals were dissolved in hot propan-2-ol (20 ml), acidified with ethereal hydrogen chloride, and evaporated in vacuo to give a foam which crystallised upon trituration with ether as the dihydrochloride three-quarter hydrate salt of the product (0.67 g) m.p. 165°–175°. (Found: C, 62.5; H, 7.6; N, 15.6. C$_{23}$H$_{31}$N$_5$O.HCl.¾H$_2$O requires C, 62.3; H, 7.6; N, 15.8%.)

EXAMPLE 25

3,N-Bis{1-[4-(2-methoxyphenyl)piperazinyl]}-2-phenylpropanamide

This compound was isolated as a side-product from the react ion following the procedure of Example 6 but substituting t-butylamine for aniline. The dihydrochloride trihydrate of the product was produced by standard methods as colourless crystals, m.p. 180°–190° (dec.) (Found: C, 57.9; H, 7.3; N, 8.3. C$_{31}$H$_{38}$N$_4$O$_3$.2HCl.3H$_2$O requires C, 58.0; H, 7.2; N, 8.7%.)

EXAMPLE 26

2-Methylpropyl 3-{1-[4-(2-methoxyphenyl)piperazinyl]}-2-phenylpropanoate

Step 1: 2-Methylpropyl 2-phenylpropenoate

This compound was isolated as a side-product from the reaction described in Example 3 as a colourless oil (1.03 g) and was used without further purification in Step 2.

Step 2: 2-Methylpropyl 3-{1-[4-(2-methoxyphenyl)piperazinyl]}-2-phenylpropanoate A solution of the product of Step 1 (0.97 g, 4.7 mmol) and 1-(2-methoxyphenyl)piperazine (0.91 g, 4.7 mmol) in propanol (10 ml) was maintained at room temperature for 90 hours and evaporated in vacuo. The residue was purified by chromatography (silica; di-iso-propyl ether) to give an oil. The oil was dissolved in propan-2-ol (10 ml) and the solution acidified with ethereal hydrogen chloride and evaporated in vacuo. The solid was triturated with ether to give the dihydrochloride salt of the product (1.173 g) m.p. 208°–212°. (Found: C, 61.6; H 7.6; N, 5.8. C$_{24}$H$_{32}$N$_2$O$_3$2HCl requires C, 61.4; H, 7.3; N, 6.0%.)

EXAMPLE 27

Ethyl 3-{1-[4-(2-methoxyphenyl)piperazinyl]}-2-phenylpropanoate

This compound was isolated as a side-product from the reaction described in Example 9. The dihydrochloride salt of the product, mp. 220°–222° was produced in the conventional manner. (Found: C, 59.5; H, 6.9; N, 6.5. C$_{22}$H$_{28}$N$_2$O$_3$2HCl requires C, 59.9; H, 6.85; N, 6.35%).

EXAMPLE 28

2-{1-[4-(2-Methoxyphenyl)piperazinyl]methyl}-N-methyl-3-phenypropanamide

This compound was prepared from the acid of Example 2 (2.00 g, 5.65 mmol) 1,1′-carbonyldiimidazole (0.92 g, 5.65 mmol), and methylamine solution, approx 33% w/w in industrial methylated spirit (0.58 g, ca 6.2 mmol) using the processes outlined in Example 6. The hydrochloride hydrate salt of the product was isolated as crystals (0.73 g), m.p. 186.5°–188.5° (from methyl acetate-ether). (Found: C, 62.8; H, 7.6; N, 10.0. C$_{22}$H$_{29}$N$_3$O$_2$.HCl.H$_2$O requires C, 62.6; H, 7.9; N, 10.0%.)

EXAMPLE 29

Ethyl 2-{1-[4-(2-methoxyphenyl)piperazinyl]methyl}-3-phenylpropanoate

This compound was prepared from the acid of Example 2 (2.00 g, 5.65 mmol) by a method analogous to that described in Example 28 with the exception that excess ethanol was used in place of methylamine. The dihydrochloride quarter hydrate salt of the salt (1.20 g) was isolated as crystals, m.p. 197°–201°. (Found: C, 60.2; H, 7.3; N, 6.0. C$_{23}$H$_{30}$N$_2$O$_3$.2HCl.¼H$_2$O requires C, 60.1; H, 7.1; N, 6.1%.)

EXAMPLES 30–36

The following 3-{1-[4-(2-methoxyphenyl)piperazinyl]}-2-phenypropanamides were prepared following the procedure of Example 6, but using the indicated amine reactant instead of aniline.

| | 3-{1-[4-(2-Methoxyphenyl)piperazinyl]}-2-phenylpropanamides | | | | | | |
|---|---|---|---|---|---|---|---|
| | | | | Found % (Required) | | | m.p. |
| Example | Amine Reactant | Amide Product | Formula | C | H | N | (°C.) |
| 30 | 3,3-dimethyl-butylamine | (3,3-dimethyl)-butylamide | C$_{26}$H$_{37}$N$_3$O$_2$.2HCl | 62.6 (62.9) | 8.0 (7.9) | 8.5 (8.5) | 187–193 |
| 31 | cyclopropyl-amine | cyclopropyl-amine | C$_{23}$H$_{29}$N$_3$O$_2$.HCl | 60.7 (60.5) | 7.2 (7.0) | 9.2 (9.2) | 193–195 |
| 32 | pyrrolidine | c | C$_{24}$H$_{31}$N$_3$O$_2$.2HCl. 0.25H$_2$O | 61.4 (61.3) | 7.4 (7.2) | 9.0 (8.9) | 212–213 |
| 33 | piperidine | d | C$_{25}$H$_{33}$N$_3$O$_2$.1.75HCl | 63.7 (63.7) | 7.5 (7.4) | 8.8 (8.9) | 191–194 |
| 34 | hexamethylene-imine | e | C$_{26}$H$_{35}$N$_3$O$_2$.1.5HCl | 65.75 (65.6) | 7.9 (7.9) | 8.8 (8.8) | 203–204 |
| 35 | cyclooctyl-amine | cyclooctylamide | C$_{28}$H$_{39}$N$_3$O$_2$.2HCl | 64.3 (64.3) | 7.9 (7.9) | 8.0 (8.0) | 204–206 |
| 36 | cyclododecyl- | cyclododecyl- | C$_{32}$H$_{47}$N$_3$O$_2$.2HCl. | 66.0 | 8.5 | 7.2 | 184–188 |

| | | 3-{1-[4-(2-Methoxyphenyl)piperazinyl]}-2-phenylpropanamides | | | | | |
|---|---|---|---|---|---|---|---|
| Example | Amine Reactant | Amide Product | Formula | Found % (Required) | | | m.p. (°C.) |
| | | | | C | H | N | |
| | amine | amide | 0.25H₂O | (65.9) | (8.6) | (7.2) | |

$^c$1-{3-{1-[4-(2-methoxyphenyl)piperazinyl]}-2-phenylpropionyl]pyrrolidine
$^d$1-{3-{1-[4-(2-methoxyphenyl)piperazinyl]}-2-phenylpropionyl]piperidine
$^e$2,3,4,5,6,7-hexahydro-1-{3-{1-[4-(2-methoxyphenyl)piperazinyl]}-2-phenylpropionyl]-1H-azepine

EXAMPLE 37

(S)-N-[2-[1-[4-(2-Methoxyphenyl)piperazinyl]]-1-phenylethyl]cyclohexanecarboxylic acid amide A solution of (S)-2-{1-[4-(2-methoxyphenyl)piperazinyl]}-1-phenylethylamine (1.03 g, 3.3 mmol) in dichloromethane (50 ml) was treated with cyclohexanecarboxylic acid chloride (0.5 ml, 3.7 mmol), after 40 minutes washed with 0.1 N-NaOH (100 ml), dried (MgSO₄), evaporated in vacuo, and the residual oil purified by column chromatography [silica; di-isopropyl ether→ether] to give the product free base (0.83 g) as white crystals.

The crystals were dissolved in hot propan-2-ol, acidified with ethereal hydrogen chloride, evaporated in vacuo, and the resulting pink crystals dried in vacuo at 70° for 24 hours to give the title compound as the hydrochloride hydrate, m.p. 141°-143°. (Found: C, 65.7; H, 8.0; N, 9.2. $C_{26}H_{35}N_3O_2.HCl.H_2O$ requires C, 65.6; H, 8.05; N, 8.8%.)

EXAMPLE 38

O-[2-[1-(4-(2-Methoxyphenyl)piperazinyl)]-1-phenylethyl]-N-cyclohexylcarbamate

Tributyltin methoxide (0.05 ml) was added to a solution of 2-[1-(4-(2-methoxyphenyl)piperazinyl)]-1-phenylethanol (1.00 g, 3.2 mmol) and cyclohexylisocyanate (0.44 g, 3.5 mmol) in dry toluene (10.0 ml). The reaction mixture was stirred at room temperature overnight and the suspension was treated with dichloromethane to afford a solution which was chromatographed on silica gel, gradient eluting with hexane ethyl acetate (2:1 to 1:2) to afford a white solid. The solid was dissolved in ethyl acetate and the solution acidified with ethereal hydrogen chloride to afford the title compound as the dihydrochloride semihydrate (1.3 g), m.p. 182.4°-186.3°. (Found: C, 60.4; H, 7.2; N, 8.0. $C_{26}H_{35}N_3O_3.2HCl.\frac{1}{2}H_2O$ requires C, 60 1; H, 7.4; N, 8.1%.)

EXAMPLE 39

O-[2-[1-[4-(2-Methoxyphenyl)piperazinyl]]-1-phenylethyl]-N-phenylcarbamate

The above compound was prepared following the procedure of Example 38 but substituting phenylisocyanate for cyclohexylisocyanate. The product was obtained as the dihydrochloride, m.p. 189.4°-191.7°.

EXAMPLE 40

2-{1-[4-(2-Methoxyphenyl)piperazinyl]}-1-phenylethyl cyclohexanecarboxylate

2-[1-(4-(2-Methoxyphenyl)piperazinyl)]-1-phenyl ethanol dihydrochloride (1.50 g, 3.9 mmol) was treated with cyclohexanecarbonyl chloride prepared from the corresponding acid (1.0 g, 7.8 mmol) by reaction with thionyl chloride in chloroform and diisopropylethylamine (2.26 g, 17.5 mmol) in chloroform (15 ml). The crude product was chromatographed and the oil obtained was dissolved in acetonitrile and acidified with ethereal hydrogen chloride to afford the title compound as the dihydrochloride, m.p. 213.2°-217.4°. (Found: C, 63.0; H, 7.3; N, 5.6. $C_{26}H_{34}H_2O_3.2HCl$ requires C, 63.0; H, 7.3; N, 5.7%.)

EXAMPLE 41

(S)-1-[2-[4-(2-Methoxyphenyl)piperazin-1-yl]-1-phenylethyl]-3-phenylurea

Phenyl isocyanate (0.45 ml, 4.2 mmol) was added to (S)-2-[1-[4-(2-methoxyphenyl)piperazinyl]]-1-phenylethylamine in dry tetrahydrofuran (10 ml) at 0° under an atmosphere of nitrogen. The solution was warmed to room temperature and after 18 hours evaporated in vacuo. The residue was chromatographed (silica; ether), dissolved in methanol, acidified with ethereal hydrogen chloride, and evaporated in vacuo to give a foam. Crystallisation from ethyl acetate propan-2-ol gave the product as the hydrochloride (0.572 g), m.p. 165°-170° (dec.). (Found: C, 63.8; H, 7.0; N, 11.1. $C_{26}H_{30}N_4O_2.1\frac{3}{8}HCl$ requires C, 63.8; H, 6.5; N, 11.4%.)

EXAMPLE 42

Ethyl (S)-N-[2-[1-[4-(2-methoxyphenyl)piperazin-yl]]-1-phenylethyl]carbamate (S)-2-[1-[4-(2-methoxyphenyl)piperazinyl]]-1-phenylethylamine (0.94 g, 3.0 mmol) in dichloromethane (20 ml) was treated with ethyl chloroformate (0.4 ml, 4.2 mmol), and after 4 days evaporated in vacuo. The residue was chromatographed, dissolved in ethanol, acidified with constant boiling hydrobromic acid, and evaporated in vacuo to give an oil. Crystallisation from ethyl acetate-propan-2-ol gave the product as the dihydrobromide (0.08 g), m.p. 170°-180° (dec.). (Found: C, 48.6; H, 6.0; N, 7.4. $C_{22}H_{29}N_3O_3.2HBr$ requires C, 48.5; H, 5.7; N, 7.7%.)

EXAMPLE 43

Methyl 3-[1-[4-(2-methoxyphenyl)piperazinyl]]-2-phenylpropionate 1,1'-Carbonyldiimidazole (1.62 g, 10.0 mmol) was added to a stirred suspension of 3-[1-[4-(2-methoxyphenyl)piperazinyl]]-2-phenylpropionic acid (3.40 g, 10.0 mmol) in dry tetrahydrofuran (40 ml). The mixture was stirred at room temperature for 1 hour and methanol (40 ml, 32 g, 990 mmol) was added. The solution was stirred at room temperature for 18 hours, and was concentrated in vacuo to give a pale yellow oil. The product was chromatographed on silica with eluant ether to give the title compound as the free base (2.37 g). A portion of the product (0.65 g) was dissolved in ethyl acetate (30 ml) and the solution was acidified with ethereal hydrogen chloride (5 ml). The mixture was concentrated in vacuo, the product was dissolved in methanol, and the solution was concentrated in vacuo. The product was triturated with acetonitrile to give the title compound as the dihydrochloride (691 mg), m.p. 211°–212°. (Found: C, 58.8; H, 6.9; N, 6.3. $C_{21}H_{26}N_2O_3.2HCl$ requires C, 59.0; H, 6.6; N, 6.5%.)

EXAMPLE 44

N-(1-Ethylpropyl)-3-[1-[4-(2-methoxyphenyl)-piperazinyl]]-2-phenylpropionamide 1,1'-Carbonyldiimidazole (649 mg, 4.0 mmol) was added to a stirred suspension of 3-[1-[4-(2-methoxyphenyl]piperazinyl]]-2-phenylpropionic acid (1.36 g, 4.0 mmol) in dry tetrahydrofuran (20 ml). The mixture was stirred at room temperature for 1 hour, and 1-ethylpropylamine (0.6 ml, 0.45 g, 5.1 mmol) was added dropwise. The mixture was stirred at room temperature for 18 hours, and was concentrated in vacuo to give a white semi solid. The product was chromatographed on silica with eluant ethyl acetate to give the title compound as the free base (0.90 g). The product was dissolved in ethyl acetate (45 ml), and the solution was acidified to give the dihydrochloride half hydrate (0.90 g), m.p. 204°–208°. (Found: C, 61.3; H, 7.8; N, 8.5. $C_{25}H_{35}N_3O_2.2HCl.0.5H_2O$ requires C, 61.1; H, 7.8; N, 8.55%.)

EXAMPLE 45

4-[3-[1-[4-(2-methoxyphenyl)piperazinyl]]-2-phenylpropionyl]morpholine

The above compound was prepared following the procedure of Example 44 substituting morpholine for 1-ethylpropylamine. The product was isolated as the dihydrochloride, m.p. 213°–217°.

EXAMPLE 46

1-{3-{1-[4-(2-Methoxyphenyl)piperazinyl]]-2-phenylpropionyl}azetidine 1,1-carbonyldiimidazole (0.81 g, 5 mmol) was added to a stirred suspension of 3-{1-[4-(2-methoxyphenyl)-piperazinyl]}-2-phenylpropionic acid (1.70 g, 5 mmol) in dry tetrahydrofuran (25 ml). The suspension was stirred at room temperature for 1 h, and azetidine (1.12 g, 20 mmol) was added in one portion.

After 21 h the solution was concentrated in vacuo to give a solid which was purified by chromatography (silica; ethyl acetate). The free base was dissolved in methanol, the solution was acidified with ethereal hydrogen chloride and evaporated in vacuo, and the solid triturated with acetonitrile to give the product as the dihydrochloride quarter hydrate (0.25 g), m.p. 181°–184° (Found: C, 60.4; H, 7.0; N, 9.31; $C_{23}H_{29}N_3O_2.2HCl.0.25H_2O$ requires C, 60.3; H, 6.9; N, 9.2%).

EXAMPLE 47

O-[2-[1-[4-(2-Methoxyphenyl)piperazinyl]]-1-phenylethyl}-N-(3-chlorophenyl)carbamate Tributyltin methoxide (0.10 ml) was added to a stirred solution of 2-{1-[4-(2-methoxyphenyl)-piperazinyl]}-1-phenylethanol (1.60 g, 5.1 mmol) and 3-chlorophenylisocyanate (0.87 g, 5.7 mmol) in dichloromethane (15 ml). The mixture was stirred for 70 h, filtered, and the filtrate evaporated in vacuo. The residue was purified by chromatography [silica; hexane-ethyl acetate (1:1→1:2] to afford an oil which solidified on standing. The off white solid was dissolved in acetonitrile (10 ml) and acidified with ethereal hydrogen chloride to afford the product as the one and eight-tenth hydrochloride salt (1.57 g), m.p. 159.2°–163.0° (Found: C, 58.6; H, 5.9; N, 7.9;$C_{26}H_{28}N_3O_3Cl.1.8HCl$ requires C, 58.5; H, 5.6; N, 7.9%

EXAMPLE 48

1-Ethyl-3-{2-[1-[4-(2-methoxyphenyl)piperazinyl]]-1-phenylethyl}carbonate

Ethyl chloroformate (0.60 g, 5.5 mmol) was added to a solution of 2-{1-[4-(2-methoxyphenyl)piperazinyl]}-1-phenylethanol (1.57 g, 5.0 mmol) and triethylamine (0.56 g, 5.5 mmol) in dichloromethane (15 ml). The mixture was stirred for 70 h, evaporated in vacuo, and the residue purified by chromatography [silica; hexane-ethyl acetate (1:1)] to afford an oil. The oil was dissolved in a acetonitrile (10 ml) and acidified with ethereal hydrogen chloride to afford the dihydrochloride salt of the product (0.41 g), m.p. 213°–215° (dec.) Found C, 57.6; H, 6.7; N. 6.1; $C_{22}H_{28}N_2O_4.2HCl$ requires C, 57.8; H, 6.6; N, 6.1%)

EXAMPLE 49

2-{1-[4-(2-Methoxyphenyl)piperazinyl]}-1-phenylethyl benzo-2,4-dioxin-2-ylcarboxylate Benzo-2,4-dioxin-2-ylcarboxylic acid (2.10 g, 11.7 mmol) in thionyl chloride (10.0 ml) was heated under reflux for 1 h and the excess thionyl chloride removed under reduced pressure. The crude acid chloride was dissolved in dichloromethane (10.0 ml) and a solution of 2-{1-[4-(2-methoxyphenyl)piperazinyl]}-1-phenylethanol dihydrochloride (1.50 g, 3.9 mmol) in dichloromethane (5.0 ml) added, followed by triethylamine (1.22 g, 12.1 mmol). The mixture was stirred for 18 h, filtered and the filtrate evaporated in vacuo. The oil was purified by chromatography [silica; hexane-ethyl acetate (2:1→2;3], dissolved in acetonitrile (10 ml) and acidified with ethereal hydrogen to give the product as a dihydrochloride salt (1.37 g), m.p. 202°–206° (Found C, 61.5; H, 6.0: N, 5.1.$C_{28}H_{30}N_2O_5.2HCl$ requires C, 61.4; H, 5,9; N, 5.1%)

EXAMPLE 50

(S)-8-{2-[1-[4-(2-Methoxyphenyl)piperazinyl]]-1-phenylethyl}}-8-azaspiro[4.5]decan-7,9-dione A solution of (S)-2-{1-[4-(2-methoxyphenyl) piperazinyl]}-1-phenethylamine (1.0 g, 3,2 mmol) and 3,3-tetramethyleneglutaric anhydride (0.543 g, 3,2 mmol) in pyridine (10 ml) was heated under reflux under an atmosphere of nitrogen for 21 h, cooled to room temperature, and evaporated in vacuo to give a brown oil. A solution of the oil in acetic anhydride (15 ml) was heated under reflux for 21 h, cooled to room temperature, and evaporated in vacuo. The residue in water was basified with saturated aqueous ammonia and extracted with ethyl acetate (2×50 ml). The extracts were washed with water (100 ml), dried (MgSO₄), and evaporated in vacuo. The residue was purified by chromatography [silica; hexane-ethyl acetate (3:2)] to give the product free base a yellow oil (0.82 g).

The oil was dissolved in methanol (5 ml) and the solution acidified with ethereal hydrogen chloride, evaporated in vacuo, and the crystals triturated with ether to give the dihydrochloride salt of the product (0.63 g) m.p. 203°–206° (Found: C, 62.9; H, 7.0; N, 7.9;.C$_{28}$H$_{35}$N$_3$O$_3$.2HCl requires C, 62.5; H, 7.1; N, 8.0%).

EXAMPLE 51

2,3,4,5,6,7-Hexahydro-1-{2-[1-(4-(2-methoxyphenyl)piperazinyl)methyl]-3-phenylpropanoyl}-1H-azepine This compound was prepared from the acid of Example 2 (20 g, 5.65 mmol); 1,1'-carbonyldiimidazole (0.92 g, 5.7 mmol), and hexahydro-1H-azepine (0.62 g, 6.3 mmol) using the method outlined in Example 6 and the crude product was purified by chromatography [silica; ethyl acetate-hexane (1:1)]. The sesquihydrochloride salt of the product was isolated as crystals (0.96 g), m.p. 195°–195.5° (from ethyl acetate). (Found: C, 65.9; H, 8.0; N, 8.5. C$_{27}$H$_{37}$N$_3$O$_2$.1½HCl requires C, 66.1; H, 7.9; N,8.6%)

EXAMPLE 52

N-Cycloheptyl-2-{1-[4-(2-methoxyphenyl)piperazinyl]methyl}-3-phenylpropanamide

This compound was prepared from the dihydrochloride salt of the acid of Example 2 (2.2 g, 4.5 mmol), 1,1'-carbonyldiimidazole (0.8 g, 4.9 mmol), and cycloheptylamine (0.56 g, 4.9 mml) in the presence of triethylamine (1.18 g, 11.7 mmol) using the method outlined in Example 51. The dihydrochloride salt of the product was isolated as off white crystals (0.91 g), m.p. 178.5°–181.5°. (Found: C, 64.1; H, 7.9; N, 8.0. C$_{28}$H$_{39}$N$_3$O$_2$.2HCl requires C, 64.4; H, 7.9; N, 8.0%).

EXAMPLE 53

(a)
1-{1-[4-(2-Methoxyphenyl)piperazinyl]}-3,3-dimethyibutan-2-ol

A mixture of 1-(2-methoxyphenyl)piperazine hydrochloride (34.5 g, 0.16 mol), 3,3-dimethyl-1,2-epoxybutane (20 g, 0.2 mol) triethylamine (20 g), and acetonitrile (120 mol) was heated at reflux for 56 h. The reaction was then diluted with water (500 ml) and extracted with ether (200 ml). The extract was washed with water (2×200 ml), dried (sodium sulphate), and evaporated in vacuo. The residue was dissolved in ethanol (100 ml) and ether (50 ml) and the solution acidified with ethanolic hydrogen chloride to precipitate the dihydrochloride salt of the product (26.1 g), m.p. 243°–245°.

(b)
2-{1-[1-(4-(2-Methoxyphenyl)piperazinyl]-3,3-dimethyl}butyl-4-fluorobenzoate The dihydrochloride salt of the product of Example 53(a) (1.0 g, 2.7 mmol), triethylamine (0.4 g, 3.8 mmol), and 4-fluorobenzoyl chloride (0.6 g, 3.8 mmol) in dichloromethane (15 ml) was stirred at room temperature for 18 h and the reaction mixture concentrated in vacuo. The residue was purified by chromotagraphy [silica; ethyl acetate-hexane (1:1)] to afford an oil which was dissolved in ethyl acetate and acidified with ethereal hydrogen chloride to afford the dihydrochloride salt of the product, m.p. 232.5°–234°. (Found: C, 58.9; H, 6.9; N, 5.6. C$_{24}$H$_{31}$FN$_2$O$_3$ requires C 59.1; H, 6,8; N, 5.8%).

EXAMPLE 54

N-Cyclopropyl-2-{1-[4-(2-methoxyphenyl)piperazinyl]methyl}-3-phenylpropanamide

This compound was prepared from the acid of Example 2 (2.5 g, 7.0 mmol), 1,1'-carbonyldiimidazole (1.2 g, 7.4 mol) and cyclopropylamine (0.44 g, 7,7 mmol) using the method outlined in Example 51. The hydrochloride quarter hydrate salt of the product was isolated as powder (2.12 g,), m.p. 169°–170.5° (Found: C, 66.3; H 7.61; N, 9.4. C$_{24}$H$_{31}$N$_3$O$_2$.HCl.¼H$_2$O requires C 66.3; H, 7.5; N, 9.7%).

EXAMPLE 55

(a) α-{[1-(4-Phenylpiperazinyl)]methyl}benzeneacetic acid

1-Phenylpiperazine and atropic acid in ethanol is heated under reflux for 18 h, cooled to room temperature, and evaporated in vacuo. The solid is triturated with acetone to give the title product.

(b)
N-Cyclopropyl-2-phenyl-3-[1-(4-phenylpiperazinyl)]-propanamide

This compound is prepared by the reaction-of the product of Example 55(a) with 1,1'-carbonyldiimidazole and cyclopropylamine following the procedure outlined in Example 6.

EXAMPLE 56

N-cyclohexyl-2-phenyl-3-{1-[4-(3-trifluoromethylphenyl) piperazinyl]}propanamide A solution of the product of Example 4 and N-(3-trifluoromethylphenyl)piperazine is heated in propanol in the presence of a small quantity of acetic acid as catalyst to give the title product.

EXAMPLE 57

(a) 2-{1-[4-(1-Naphthyl)piperazinyl]}-1-phenylethanol

Styrene oxide and 1-(1-naphthyl)piperazine in acetonitrile are heated under reflux. Concentration in vacuo and purification by chromatography (silica; ethyl acetate) gives the product.

(b) 2-{1-[4-(1-Naphthyl)piperazinyl]}-1-phenylethyl cyclohexananecarboxylate

This compound is prepared by the reaction of the product of Example 57(a) with cyclohexanecarbonyl chloride using the method described in Example 40

EXAMPLE 58

(a) 2-{1-[4-(3-Chlorophenyl)piperazinyl]}-1-phenyl ethanol

The reaction of styrene oxide and 1-(3-chlorophenyl)-piperazine gives the title compound using the method outlined in Example 57(a).

(b) 0-{2-[1-(4-(3-Chlorophenyl)piperazinyl)]-1-phenyl ethyl}-N-phenylcarbamate

The above compound in prepared following the procedure of Example 38 but substituting phenylisocyanate for cyclohexylisocyanate and the product of Example 58 (a) for 2-[4-(2-methoxyphenyl)piperazin-1-yl]-1-phenylethanol.

EXAMPLE 59

2,3,4,5,6,7-Hexahydro-1-{4-[1-[4-(2-methoxyphenyl)-piperazinyl]]-2-phenylbutyryl}-1H-azepine Butyl lithium (1.5M in hexane: 5 ml, 7.5 mmol) was added dropwise over 5 min, maintaining the temperature below 8° C., to a stirred solution of 2,3,4,5,6,7-hexahydro-1-phenylacetyl-1H-azepine (1.48 g, 6.8 mmol)

and diisopropylamine (2.0 ml, 1.4 g, 14 mmol) in dry toluene (16 ml) under argon. The mixture was stirred at 0° C. for 1 h, and a solution of freshly chromatographed 1-(2-chloroethyl)-4-(2-methoxyphenyl)piperazine (1.73 g, 6.8 mmol) in dry toluene (4 ml) was added dropwise. The mixture was stirred at 0° C. to 20° C. for 18 h, and water (50 ml) was added. The layers were separated, and the aqueous phase was extracted with ethyl acetate (2×50 ml). The combined organic phases were concentrated in vacuo. The crude product (2.91 g) was chromatographed on silica with eluant ethyl acetate to give the title compound as the free base (0.15 g). The product was dissolved in ethyl acetate (30 ml), and the solution was acidified with ethereal hydrogen chloride. The product was collected to give the title compound as the dihydrochloride three quarters hydrate (0.36 g), m.p. 175°-178° C. (Found: C, 62.05; H, 7.8; N, 7.75. $C_{27}H_{37}N_3O_2 \cdot 2HCl \cdot 0.75 H_2O$ requires C, 62.1; H, 7.8; N, 8.05%).

EXAMPLE 60

Resolution of 2,3,4,5,6,7-hexahydro-1-{4-[1-[4-(2-methoxyphenyl)-piperazinyl]]-2-phenylbutyryl}-1-H-azepine (a) 2,3,4,5,6,7-Hexahydro-1-{4-[1-[4-(2-methoxyphenyl)-piperazinyl]]-2-phenylbutyryl}-1H-azepine (12.1 g) was dissolved in ethyl acetate (2.5 volumes, ie 30 ml) and a solution of dibenzoyl-L-tartaric acid monohydrate (1 mol eq) in ethyl acetate (2.5 volumes) added. The initially formed oil was redissolved by the addition of the minimum quantity of acetonitrile (3.6 ml). After 3 d, filtration gave crystals (6.2 g) which had an optical purity of 28% as judged by chiral H.P.L.C. Recrystallisation first from ethyl acetate-acetonitrile (3:10, 1,3 volumes), which gave a sample with an optical purity of 84%, and secondly from methanol (7.5 volumes) gave the first enantiomer (isomer I) of the product as a dibenzoyl-L-tartrate (2.1 g) m.p. 147°-150° C., $[\alpha]_D^{22} = -26°$ (1% in MeOH) (Found: C, 66.7; H, 6.7; N, 5.1 $C_{27}H_{37}N_3O_2 \cdot C_{18}H_{14}O_8 \cdot H_2O$ requires C, 66.6; H, 6.6; N, 5.2%) with an optical purity of 97.4%. The sample was converted to the free base of isomer (I) (1.1 g), $[\alpha]_D^{26} = +53°$ (1% in CHCl₃) and thence to the hydrochloride salt in the usual manner to afford a colourless powder (0.65 g), m.p. 181°-184° C., $[\alpha]_D^{23} = +35°$ (1% in MeOH) (Found: C, 63.1; H, 7.8; N, 7.9. $C_{27}H_{37}N_3O_2 \cdot 2HCl \cdot 0.25H_2O$ requires C, 63.2; H, 7.7; N, 8.2%) with an optical purity of 97.6%.

(b) The second enantiomer (isomer II) was formed in a similar manner from the racemate of Example 1 and dibenzoyl-D-tartaric acid monohydrate. Isomer II dibenzoyl-D-tartrate m.p. 141°-142° C., $[\alpha]_D^{25} = +25°$ (1% in MeOH)

(Found: C, 67.3; H, 6.7; N, 5.2. $C_{27}H_{37}N_3O_2 \cdot C_{18}H_{14}O_8 \cdot 0.25H_2O$ requires C, 67.3; H, 6.5; N, 5.2%).

Isomer II base $[\alpha]_D^{26} = -62°$ (1% solution in CHCl₃)
Isomer II hydrochloride m.p. 181°-184° C., $[\alpha]_D^{26} = -36°$ (1% in MeOH)

(Found: C, 60.2; H, 7.7; N, 7.75 $C_{27}H_{37}N_3O_2 \cdot 2HCl \cdot 1.75H_2O$ requires C, 60.05; H, 7.9; N, 7.8%) with an optical purity of 98.2%.

I claim:

1. A compound of the formula

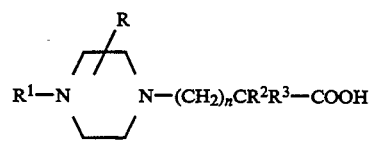

III wherein n is one of the integers 1 or 2,

R is hydrogen or lower alkyl, $R^1$ is a phenyl or naphthyl radical optionally substituted by one or more lower alkyl, lower alkoxy, halogen, trifluoromethyl, nitro, carbalkoxy, carboxamido, cyano, amino, (lower)alkylamino or di(lower)alkylamino substituents; or a mono or bicyclic heteroaromatic radical having 5 to 10 ring atoms, the heteroaromatic radical having, as heteroatoms, one or two nitrogen atoms and being optionally substituted by one or more lower alkyl, lower alkoxy, halogen, trifluoromethyl, nitro, carbalkoxy, carboxamido, cyano, amino, (lower)alkylamino or di(lower)alkylamino substituents, $R^2$ is hydrogen or lower alkyl, and $R^3$ is an aryl radical, or an aryl(lower)alkyl radical, in which the aryl radical is a phenyl or naphthyl radical optionally substituted by one or more lower alkyl, lower alkoxy, halogen, trifluoromethyl, nitro, carbalkoxy, carboxamido, cyano, amino, (lower)alkylamino or di(lower)alkylamino substituents.

2. A compound according to claim 1 in which $R^1$ is a phenyl radical optionally substituted by one or more lower alkoxy, halogen, trifluoromethyl, nitro, carbalkoxy, carboxamido, cyano, amino, (lower)alkylamino or di(lower)alkylamino substituents.

3. A compound according to claim 1 in which $R^3$ is a phenyl radical optionally substituted by one or more lower alkoxy, halogen, trifluoromethyl, nitro, carbalkoxy, carboxamido, cyano, amino, (lower)alkylamino or di(lower)alkylamino substituents.

4. A compound according to claim 1 which is α-[1-[4-(2-methoxyphenyl)piperazinyl]methyl]benzeneacetic acid.

5. A compound according to claim 1 which is 2-[1-[4-(2-methoxyphenyl)piperazinyl]methyl]-3-benzene propanoic acid.

* * * * *